(12) United States Patent
Odland

(10) Patent No.: US 8,388,584 B2
(45) Date of Patent: Mar. 5, 2013

(54) METHOD AND SYSTEM FOR THE USE OF HOLLOW FIBER CATHETERS IN TOPICAL APPLICATIONS

(75) Inventor: Rick M. Odland, Roseville, MN (US)

(73) Assignee: Twin Star Medical, Inc., Minneapolis, MN (US)

( * ) Notice: Subject to any disclaimer, the term of this patent is extended or adjusted under 35 U.S.C. 154(b) by 531 days.

(21) Appl. No.: 12/525,683

(22) PCT Filed: Feb. 8, 2008

(86) PCT No.: PCT/US2008/053483
§ 371 (c)(1),
(2), (4) Date: Aug. 4, 2009

(87) PCT Pub. No.: WO2008/098207
PCT Pub. Date: Aug. 14, 2008

(65) Prior Publication Data
US 2010/0100061 A1   Apr. 22, 2010

Related U.S. Application Data

(60) Provisional application No. 60/889,077, filed on Feb. 9, 2007.

(51) Int. Cl.
*A61M 1/00* (2006.01)
(52) U.S. Cl. ............... 604/313; 604/19; 604/27; 604/9
(58) Field of Classification Search ............ 604/313, 604/9, 19, 27
See application file for complete search history.

(56) References Cited

U.S. PATENT DOCUMENTS

| | | | |
|---|---|---|---|
| 5,036,643 A | 8/1991 | Bodolay | |
| 5,304,136 A * | 4/1994 | Erskine et al. | 604/110 |
| 5,645,081 A | 7/1997 | Argenta | |
| 6,030,358 A | 2/2000 | Odland | |
| 6,458,109 B1 * | 10/2002 | Henley et al. | 604/304 |
| 6,537,241 B1 * | 3/2003 | Odland | 604/9 |
| 6,942,633 B2 | 9/2005 | Odland | |
| 6,942,634 B2 | 9/2005 | Odland | |
| 7,128,735 B2 | 10/2006 | Weston | |
| 2003/0167031 A1 | 9/2003 | Odland | |
| 2004/0243073 A1 * | 12/2004 | Lockwood et al. | 604/313 |
| 2005/0165342 A1 | 7/2005 | Odland | |
| 2006/0025727 A1 | 2/2006 | Boehringer | |
| 2007/0018096 A1 * | 1/2007 | Kawakatsu | 250/309 |
| 2007/0032763 A1 * | 2/2007 | Vogel | 604/305 |
| 2007/0060834 A1 | 3/2007 | Odland | |
| 2010/0145289 A1 * | 6/2010 | Lina et al. | 604/319 |

OTHER PUBLICATIONS

Andros et al., "Consensus statement on negative pressure wound therapy (VAC therapy) for the management of diabetic foot wounds", Ostomy Wound Management, Jun. 2006, pp. 1-32, Sup.

* cited by examiner

*Primary Examiner* — Jacqueline Stephens
*Assistant Examiner* — Andrew J Mensh
(74) *Attorney, Agent, or Firm* — Fredrikson & Byron, PA

(57) ABSTRACT

A method and system, together with corresponding apparatus and components, and corresponding kits, for use in performing topical wound therapy by using topical negative pressure (TNP) in combination with one or more hollow fiber catheters. In one embodiment, the method provides hollow fiber catheters for the removal of fluid or fluid components from the wound area by ultrafiltration. In another embodiment the hollow fiber catheters are connected to an infusion pump and used to deliver therapeutic fluids to the wound area. In yet another embodiment, a first set of hollow fiber catheters is connected to a vacuum pump and a second set is connected to an infusion pump to simultaneously remove excess tissue fluid and deliver therapeutic fluid to the wound site.

20 Claims, 11 Drawing Sheets

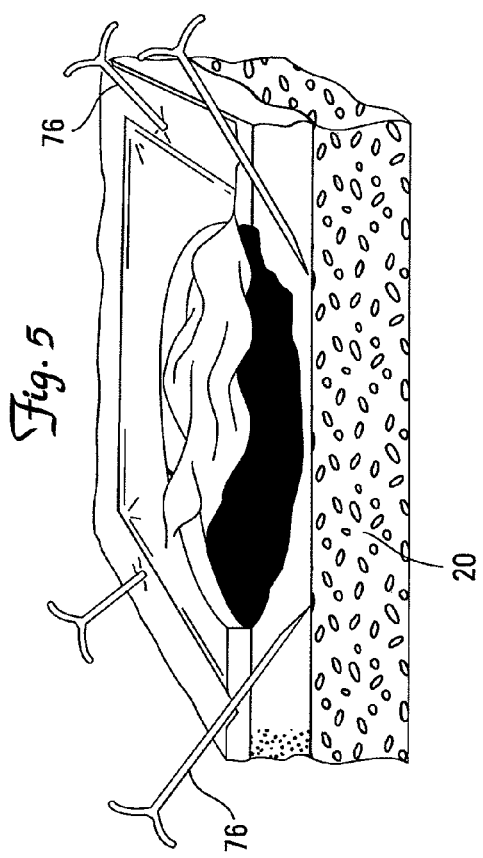
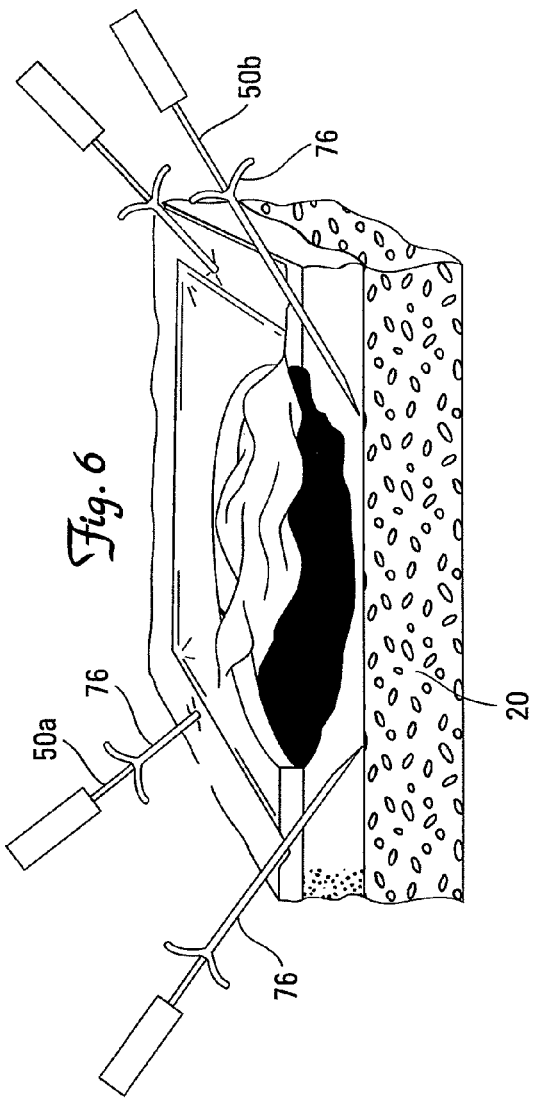

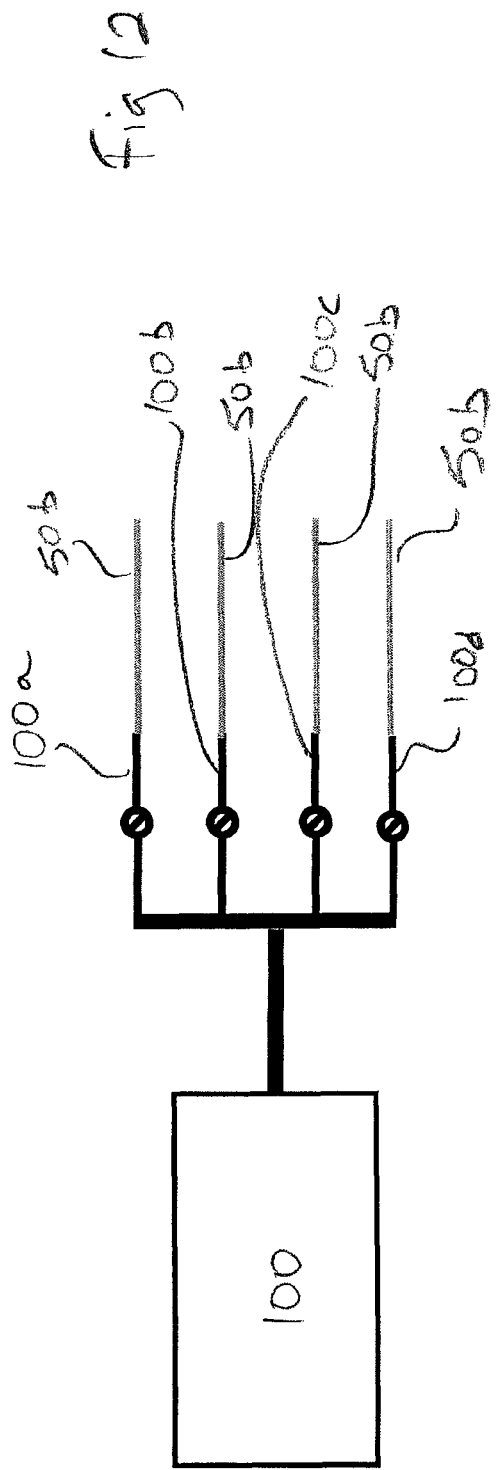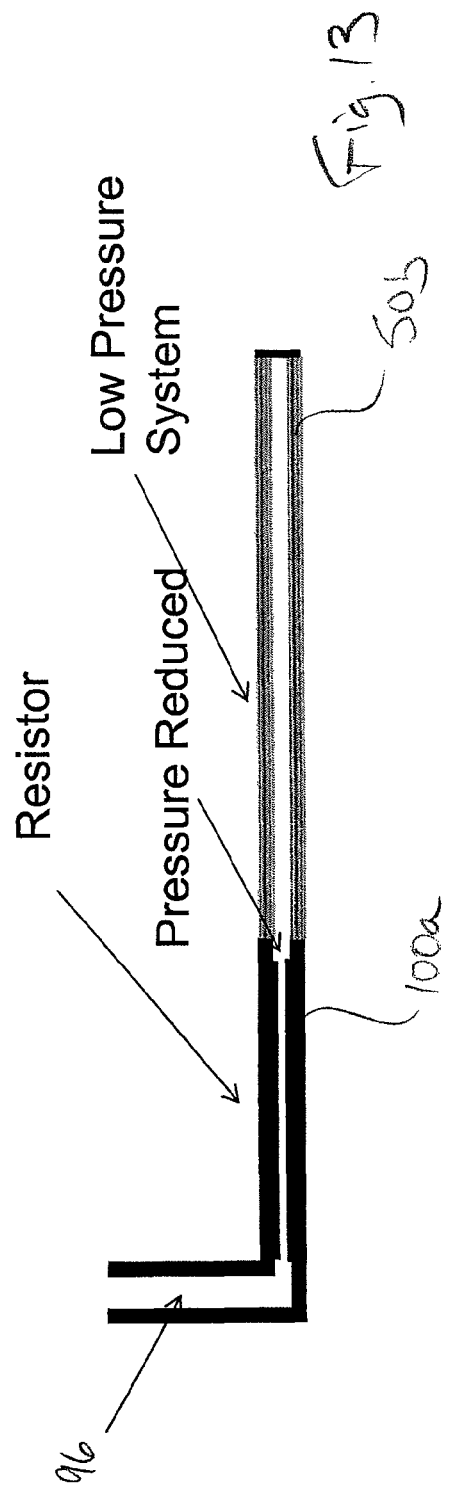

METHOD AND SYSTEM FOR THE USE OF HOLLOW FIBER CATHETERS IN TOPICAL APPLICATIONS

CROSS-REFERENCE TO RELATED APPLICATIONS

The present application claims priority to International Application No. PCT/US2008/053483 filed 8 Feb. 2008, which in turn claims priority to U.S. Provisional Application No. 60/889,077 filed 9 Feb. 2007, the teachings of all of which are incorporated herein by reference.

FIELD OF THE INVENTION

The present invention relates to the use of hollow fibers in various applications within the body. In another aspect, the invention relates to methods and apparatus to improve wound care methods and apparatus that employ topical negative pressure.

BACKGROUND

Some open wounds are sufficiently small that they will close spontaneously and heal without requiring any further force to urge the lacerated epithelial and subcutaneous tissue closer together. Larger wounds, however, are problematic in that the wound edges are too large, deep and/or far apart to spontaneously heal without additional force being applied. Problems occur where the wound is too large, deep or infected for spontaneous closing wherein a zone of stasis forms in which localized edema restricts the flow of blood into the epithelial and subcutaneous tissues near the surface of the wound. Without sufficient blood flow, the wound is unable to successfully resist bacterial infection and therefore unable to close spontaneously.

Topical negative pressure is a current standard of wound care and commands a significant market share (about 25%) among advanced wound care technologies. A relatively large drainage catheter is inserted into the wound through an incision and then covered and sealed with a plastic film. Another system, manufactured by KCI (Kinetic Concepts, Inc.) of San Antonio, Tex., used to perform topical negative pressure, involves an open cell foam member attached to a drainage catheter which is then covered with plastic film which is effective for topically draining a larger surface area. A vacuum pump is attached to the drainage catheter and negative pressure is topically applied and confined to the wound area by the plastic film. The topical method removes excess tissue fluid to promote healing and simultaneously applies a closure force to accelerate wound healing.

Since its inception well over 100 years ago, the use of topical negative pressure (TNP) therapy has today emerged as a high-technology, microprocessor controlled physical wound healing technique for use in a variety of applications, including traumatic wounds, open abdominal wounds, infected sterotomy wounds, wound bed preparation, complex diabetic wounds and skin graft fixation. Complex effects have been described at the wound/dressing interface following application of a controlled vacuum. These effects can include changes on a microscopic or molecular level and on a macroscopic tissue level, e.g., interstitial fluid flow and exudate management, edema reduction, effects on wound perfusion, protease profiles, growth factor and cytokine expression and cellular activity, all leading to enhanced granulation tissue formation and improved wound healing parameters. See, for instance, P. E. Banwell et al., "Topical Negative Pressure Wound Therapy: Mechanisms and Indications," International Wound Journal 1(2):95-106 (2004), which is incorporated by reference herein in its entirety. Various commercial apparatus exist for performing TNP. See, for instance, S. M. Jones et al., "Advances in Wound Healing: Topical Negative Pressure Therapy," Postgraduate Medical Journal 81:353-357 (2005), which is incorporated by reference herein in its entirety. See also U.S. Pat. Nos. 5,636,643 and 5,645,081 to Argenta et al., the disclosures of which are herein incorporated by reference in their entireties.

The use of a large drainage catheter removes only gross amounts of interstitial and other fluid from the wound area in the location of the placement of the drain catheter. Additional fluid which exists in the tissue around the wound area remains, inhibiting the healing process.

On a separate subject, hollow fibers can be made using various materials, e.g., from porous polymers, and have been developed for use in various ways, e.g., to improve the distribution of drugs administered directly into the central nervous system. Applicant itself has previously disclosed and claimed various applications for the use of hollow fibers in various medical applications, including microdialysis, ultrafiltration and so forth. See, for instance, U.S. Pat. Nos. 6,030,358; 6,537,241; 6,942,633; and 6,942,634; U.S. Pending application Ser. No. 10/395,573, filed Mar. 24, 2003; Ser. No. 10/508,610, filed Sep. 22, 2004; Ser. No. 11/210,072, filed Aug. 23, 2005; Ser. No. 11/492,386, filed Jul. 25, 2006; Ser. No. 11/516,447, filed Sep. 6, 2006; and Ser. No. 11/516,447, filed Sep. 6, 2006, the disclosures of each of which are incorporated herein by reference.

SUMMARY

The present invention provides a method and system, together with corresponding apparatus and components, for use in performing topical wound therapy by the use of topical negative pressure (TNP) in combination with one or more hollow fibers. The apparatus and methods can be used to improve upon the traditional methods by removing excess interstitial fluid from deeper within the wound, thus further facilitating wound healing. Additional opportunities exist for infusing various medications and other substances which are beneficial to the healing process such as wound healing agents, pain medication, antibiotics etc. Further, the method and system can be used in certain wound conditions that require simultaneous aspiration of fluid and drug infusion.

In one aspect, the present invention comprises a method for performing topical negative pressure wound care, including providing one or more drainage catheter(s) and one or more hollow fiber catheter(s). One or more drainage catheter(s) and one or more hollow fiber catheter(s) are positioned proximate a wound bed and in desired positions relative to each other. The drainage catheter(s) and hollow fiber catheter(s) can be operably connected to a vacuum pump and the vacuum pump activated to provide negative pressure to both the drainage catheter(s) and hollow fiber catheter(s) in a desired manner. In an additional step, the hollow fiber catheter(s) can be positioned by introducing a needle introducer having an introducer channel into the wound bed and inserting a hollow fiber catheter into the introducer channel of the needle introducer.

In another aspect, the present invention comprises a method for performing topical negative pressure wound care while simultaneously infusing a therapeutic fluid into the wound, including providing one or more drainage catheters and one or more hollow fiber catheters. One or more drainage catheter(s) and one or more hollow fiber catheter(s) are positioned proximate the wound bed and in desired positions relative to each other. The drainage catheter(s) are connected to a vacuum pump and the vacuum pump is activated to draw a vacuum from the drainage catheter(s). The hollow fiber catheter(s) are connected to an infusion pump which is connected to and in fluid communication with the therapeutic fluid. The infusion pump is activated to apply positive fluid pressure to the hollow fiber catheter(s), thus delivering the therapeutic fluid through the hollow fiber catheter(s). In an additional step, the hollow fiber catheter(s) are positioned by introducing a needle introducer having an introducer channel into the wound bed and inserting a hollow fiber catheter into the introducer channel of the needle introducer.

In an alternative aspect, the present invention comprises a method for performing topical negative pressure wound care while simultaneously infusing a therapeutic fluid into the wound, including providing one or more drainage catheters, at least a first hollow fiber catheter used for aspiration of fluid and at least a second hollow fiber catheter used for infusion of the therapeutic fluid. One or more drainage catheters, one or more first hollow fiber catheters and the one or more second hollow fiber catheters are positioned proximate a wound bed and in desired positions relative to each other. The drainage catheter(s) are connected to a vacuum pump and the first hollow fiber catheter(s) are connected to a vacuum pump, followed by activating the vacuum pump to provide negative pressure to both the drainage catheter(s) and hollow fiber catheter(s) in a desired manner. The second hollow fiber catheter(s) are connected to an infusion pump which is connected to and in fluid communication with the therapeutic fluid, followed by activating the infusion pump to apply positive fluid pressure to the hollow fiber catheter(s), thus delivering the therapeutic fluid through the hollow fiber catheter(s). In an additional step, the first hollow fiber catheter and second hollow fiber catheter are positioned by introducing a needle introducer having an introducer channel into the wound bed and inserting a hollow fiber catheter into the introducer channel of the needle introducer.

In a further aspect, the present invention comprises a system, and corresponding kits comprising some or all components, for use in performing topical negative pressure wound care, the system including: a vacuum pump to provide a source of negative pressure, a drainage catheter attachable to the vacuum pump for removing excess fluid from a wound bed, wound care film to protect the wound bed and confine the area of applied negative pressure, and a needle introducer to allow the introduction of a hollow fiber catheter. A control monitor is also included and has the vacuum pump in fluid communication with a first vacuum pump regulator for the drainage catheter and a second vacuum pump regulator for the hollow fiber catheter, to provide differential negative pressure required by the drainage catheter and the hollow fiber catheter.

In yet another aspect, the present invention comprises a system, and corresponding kits comprising some or all components, for use in performing topical negative pressure wound care in conjunction with fluid infusion, the system including: a vacuum pump to provide a source of negative pressure, a drainage catheter attachable to the vacuum pump for removing excess fluid from a wound bed, wound care film to protect the wound bed and confine the area of applied negative pressure, and a needle introducer to allow the introduction of a hollow fiber catheter. An infusion pump is included and provides a source of positive pressure and an infusion reservoir containing therapeutic fluid is in fluid communication with the infusion pump to deliver the therapeutic fluid to the wound bed through the hollow fiber catheter. A control monitor is also included with the vacuum pump in fluid communication with a vacuum pump regulator for the drainage catheter and an infusion pump regulator for the hollow fiber catheter.

In an additional aspect, the present invention comprises a system, and corresponding kits comprising some or all components, for use in performing topical negative pressure wound care in conjunction with fluid infusion, the system including: a vacuum pump to provide a source of negative pressure, a drainage catheter attachable to the vacuum pump for removing excess fluid from a wound bed, wound care film to protect the wound bed and confine the area of applied negative pressure, a first needle introducer to allow the introduction of a first hollow fiber catheter, the first hollow fiber catheter in fluid communication with the vacuum pump to withdraw excess fluid from the wound bed and a second needle introducer to allow the introduction of a second hollow fiber catheter. An infusion pump is included for providing a source of positive pressure, and an infusion reservoir containing therapeutic fluid is in fluid communication with the infusion pump to deliver the therapeutic fluid to the wound bed through the second hollow fiber catheter. Also included is a control monitor having the vacuum pump in fluid communication with a first vacuum pump regulator for the drainage catheter, a second vacuum pump regulator for the first hollow fiber catheter, the first and second vacuum pump regulators to provide differential levels of negative pressure required by the drainage catheter and the second hollow fiber catheter, and an infusion pump regulator for the hollow fiber catheter.

BRIEF DESCRIPTION OF THE DRAWINGS

FIG. 5 is a perspective view of the introduction of the peel away needle introducer in to the wound bed with the sheath remaining following removal of the needle.

FIG. 6 is a perspective view of hollow fiber catheters being inserted into the sheath following removal of the needle.

FIG. 12 is a schematic of the infusion distribution system.

FIG. 13 is a longitudinal cross section of an infusion output.

DETAILED DESCRIPTION

Definitions

"Catheter" is used in its general sense and refers to a conduit capable of transporting a substance or fluid to a remote location.

"Distal" means further from the point controlled by the operator (e.g., physician or technician) of a device.

"Fluid" means a substance offering no permanent resistance to change of shape, such as a gas or a liquid.

"Proximal" means closer to the point controlled by the operator (e.g., physician or technician) of a device.

"Semi-Permeable Membrane" means a porous or semi-permeable barrier permitting controlled passage of fluid molecules under certain conditions.

"Therapeutic Fluid" means medications and other substances which are beneficial to the healing process such as wound healing agents, pain medication and antibiotics.

"Topical" means relating to a particular area at the surface and immediately underneath, such as an area exposed as the result of a wound.

"μm" means micron.

| Nomenclature | |
|---|---|
| 12 | Gauze |
| 14 | Drainage Catheter |
| 16 | Wound Care Film |
| 20 | Wound Bed |
| 40 | Hollow Fiber Bundle |
| 42 | Central Member |
| 44 | Lumen (Central Member) |
| 50a | Hollow Fiber Catheter (Negative Pressure) |
| 50b | Hollow Fiber Catheter (Positive Pressure) |
| 52 | Hollow Fiber |
| 52a | Distal End of Hollow Fiber |
| 52b | Proximal End of Hollow Fiber |
| 54 | Lumen (Hollow Fiber) |
| 56 | Stylet |
| 58 | End Plug |
| 60 | Intermediate Line |
| 62 | Connector |
| 64 | Vacuum Pump |
| 66 | Vacuum Drain |
| 70 | Needle Introducer |
| 72 | Introducer Channel |
| 74 | Needle |
| 76 | Peel Away Sheath |
| 94a | Low Pressure Infusion Line |
| 94b | Low Pressure Infusion Line |
| 94c | Low Pressure Infusion Line |
| 94d | Low Pressure Infusion Line |
| 96 | High Pressure Infusion Line |
| 98 | Infusion Pump Input |
| 100 | Infusion Pump |
| 100a | Infusion Pump Output |
| 100b | Infusion Pump Output |
| 100c | Infusion Pump Output |
| 100d | Infusion Pump Output |
| 102 | Infusion Line |
| 104 | Infusion Reservoir |
| 106 | Therapeutic Fluid |
| 108 | Infusion Pump Regulator |
| 150 | Control Unit/Monitor |
| 152 | Display |
| 154 | User Input |
| 155 | Power Cord |
| 156 | Power Switch |
| 158 | AC Power Input |
| 160 | Battery Pack |
| 162 | Isolation Transformer Power Supply |
| 164 | Central Processing Unit |
| 166 | Sensor Processor |
| 168 | USB Port |
| 170 | Vacuum Regulator (Drainage Catheter) |
| 170a | Vacuum Pump Input (Drainage Catheter) |
| 170b | Vacuum Pump Input (Drainage Catheter) |
| 170c | Vacuum Pump Input (Drainage Catheter) |
| 170d | Vacuum Pump Input (Drainage Catheter) |
| 172 | Vacuum Pump Regulator (Hollow Fiber Catheter) |
| 172a | Vacuum Pump Input (Hollow Fiber Catheter) |
| 172b | Vacuum Pump Input (Hollow Fiber Catheter) |
| 172c | Vacuum Pump Input (Hollow Fiber Catheter) |
| 172d | Vacuum Pump Input (Hollow Fiber Catheter) |

Figure 1:
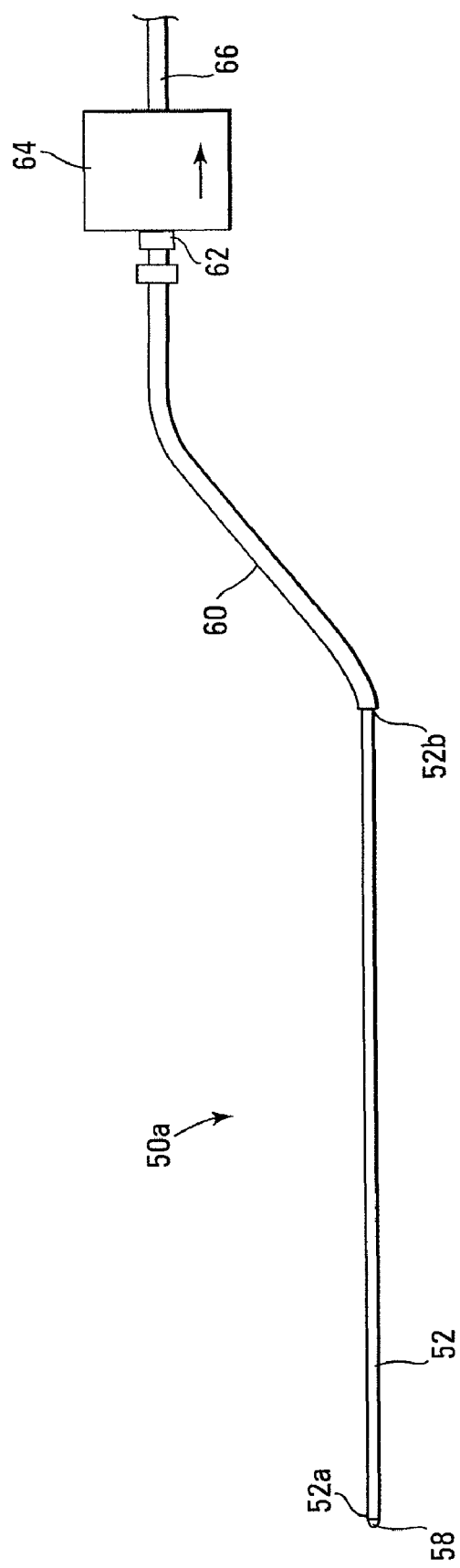
FIG. 1 is a plan view of a hollow fiber catheter of the present invention connected to a vacuum pump.
Figure 10:
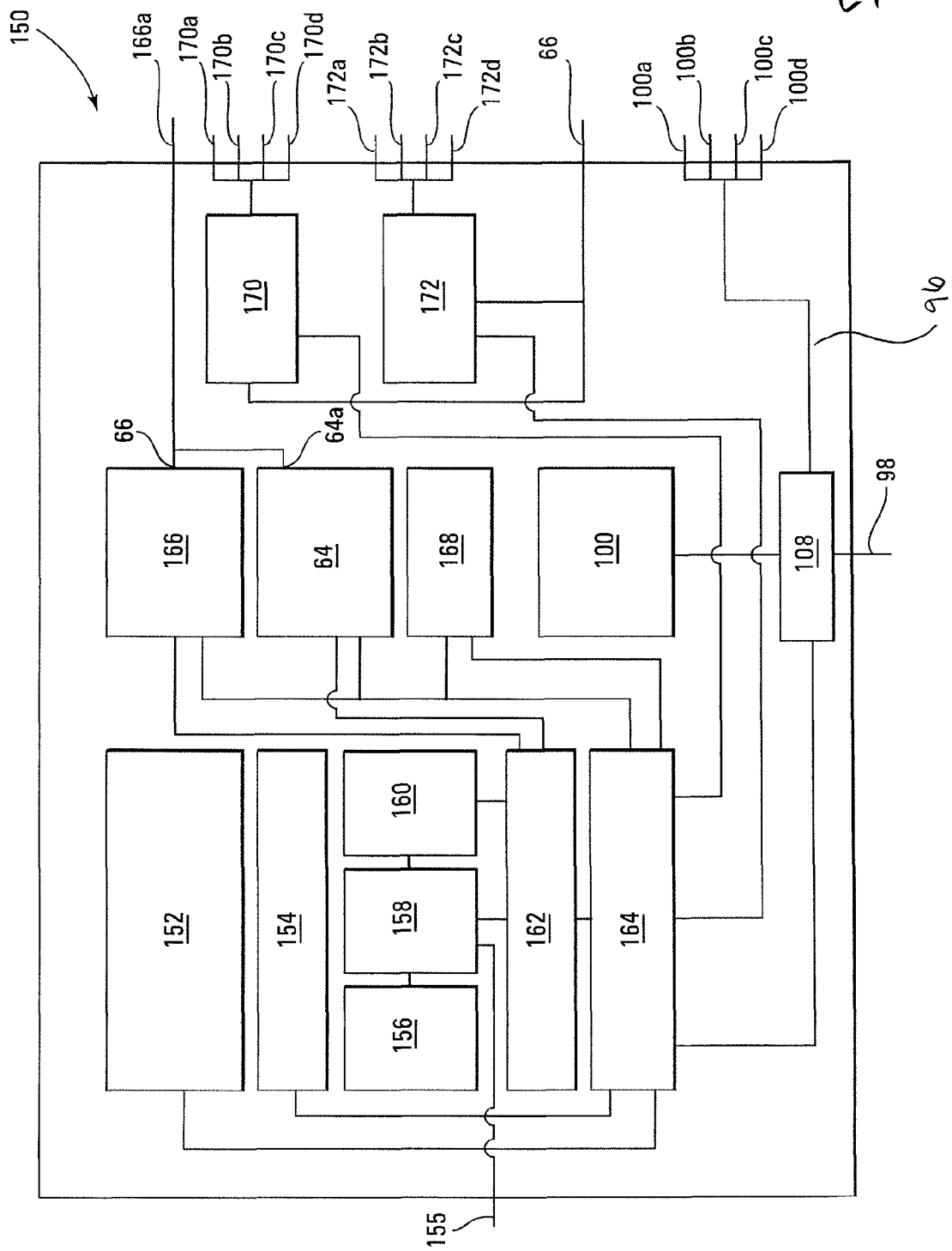
FIG. 10 is a schematic diagram of a control monitor used in conjunction with the drainage catheter and hollow fiber catheters of the invention.

FIG. 1 illustrates an embodiment of a hollow fiber catheter 50a in fluid communication with a vacuum pump 64. A hollow fiber 52 is a semi-permeable membrane and defines a distal end 52a which is provided with an end plug 58 to seal the distal end 52a, thus preventing intake of any fluid or other matter through the distal end 52a and instead allowing a more uniform intake through the pores (not shown) of the hollow fiber 52 when negative pressure is applied. The hollow fiber 52 also defines a proximal end 52b which is connected to a vacuum line 60 which proximally connects to the vacuum pump 64 by a connector 62. The vacuum pump 64 is a source of controlled negative pressure and is fitted with a vacuum drain 66 from which withdrawn fluid is collected for either disposal or analysis. An alternative embodiment comprises a hollow fiber bundle 40 as shown in FIG. 10, wherein a plurality of individual hollow fibers 52 are attached to each other surrounding a central member 42 to provide greater exposed surface area to facilitate removal of a greater volume of fluid from the wound bed 20.

Figure 1A:
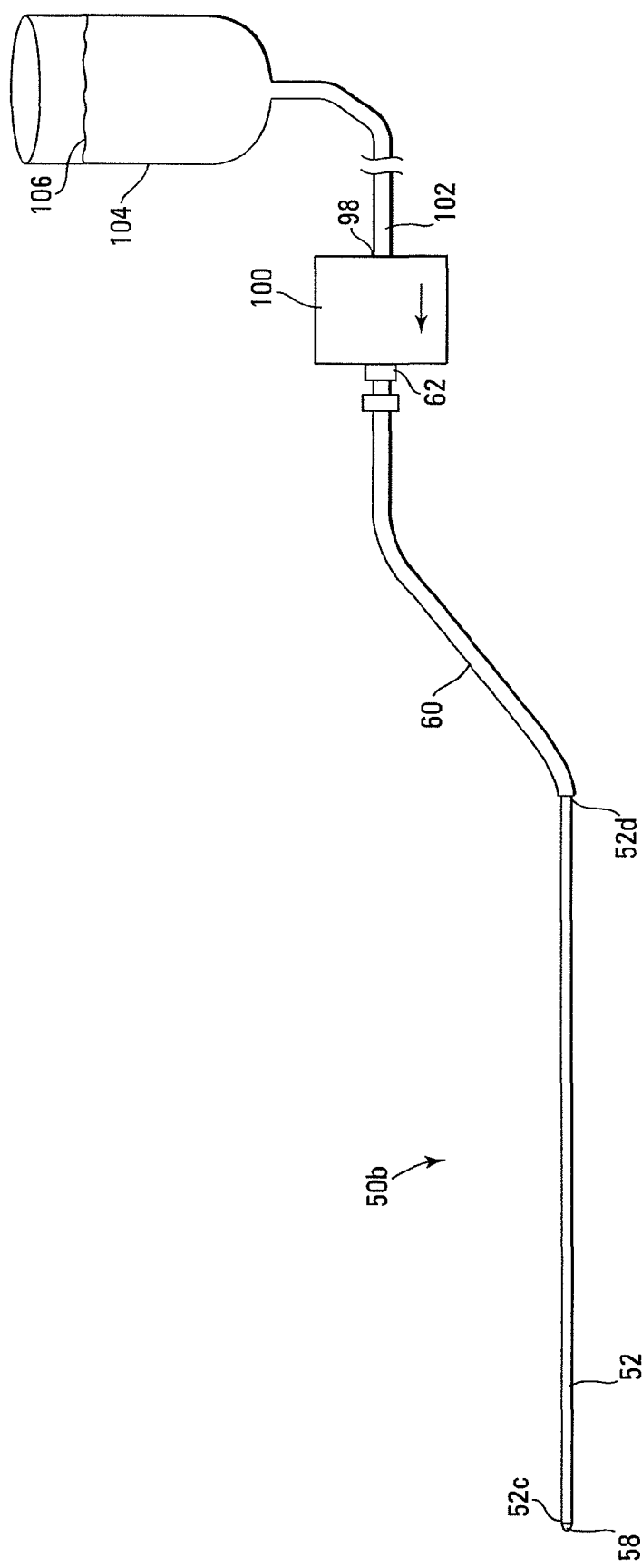
FIG. 1A is a plan view of a hollow fiber catheter of the present invention connected to an infusion pump.

FIG. 1A illustrates a hollow fiber catheter 50b in fluid communication with an infusion pump 100, and having distal and proximal ends 52c and 52d, respectively. An infusion reservoir 104 containing therapeutic fluid 106 is connected to the infusion pump 100 through an infusion line 102. The infusion pump 100 provides positive fluid pressure which moves the therapeutic fluid 106 through an intermediate line 60 into the lumen 54 of the hollow fiber 52 where it is uniformly, outwardly distributed through the pores (not shown) to a precise treatment site in the patient's body.

Figure 2:
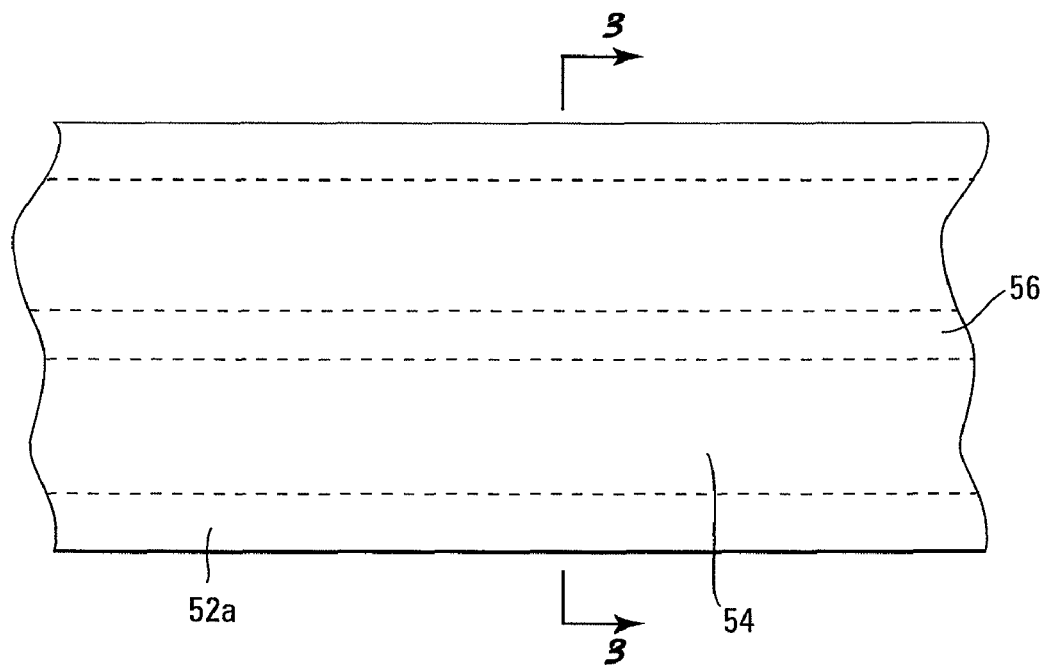
FIG. 2 is a longitudinal view of the hollow fiber using phantom lines to show underlying structures.
Figure 3:
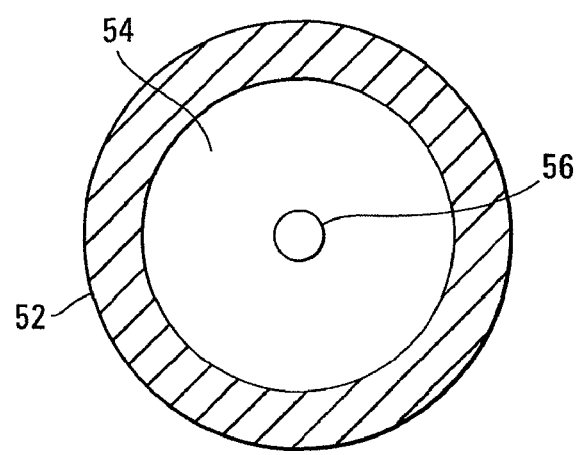
FIG. 3 is a lateral cross sectional view of the hollow fiber taken through the lines 3-3 as shown in FIG. 2.
Figure 4:
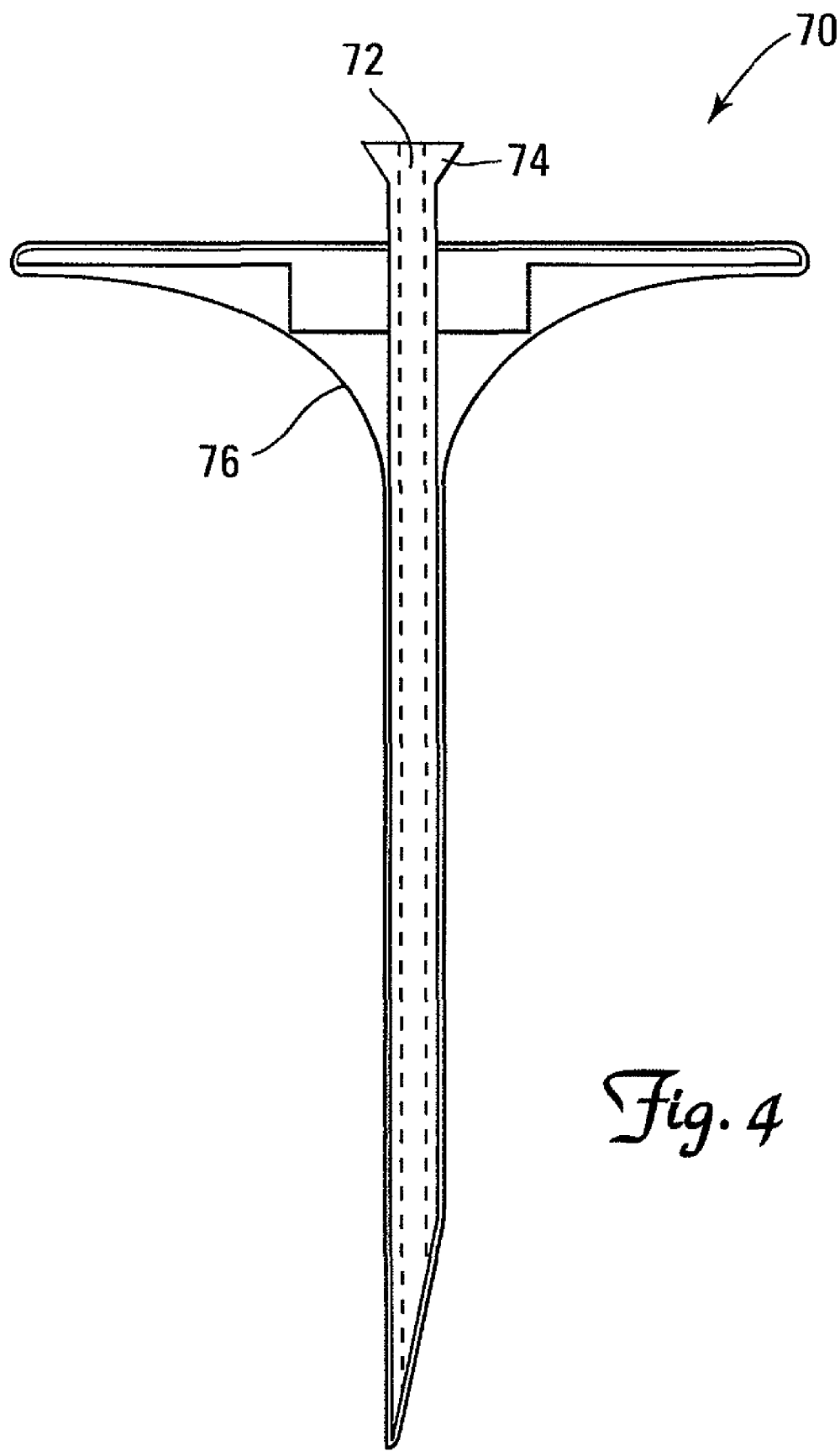
FIG. 4 is a plan view of a peel away needle introducer using phantom lines to show the introducer channel.

FIG. 2 is a longitudinal view of the hollow fiber 52 used in making the hollow fiber catheter 50a, 50b, using phantom lines to show the underlying structures. FIG. 3 is a lateral cross sectional view taken through the lines 3-3 of FIG. 2 and shows the hollow fiber 52 walls (unnumbered) which define a lumen 54 permitting fluid communication there through. It is also seen that a stylet 56 is substantially concentrically mounted within and extends the length of the hollow fiber 52. The stylet 56 provides strength and rigidity and can be made from hardened stainless steel, spring tempered steel, glass, polymeric materials or other MRI-compatible materials such as non-ferrous metals including titanium or nickel alloys. A conventional peel away needle introducer 70 as shown in FIG. 4 is used with the hollow fiber catheter 50a, 50b. The wound bed 20 or treatment site is initially accessed by the needle introducer 70, followed by insertion of the hollow fiber catheter 50a, 50b through an introducer channel 72 extending the length of the needle introducer 70. Prior to introduction of the hollow fiber catheters 50a, a conventional peel away needle introducer 70 as shown in FIG. 4 is inserted into the wound bed 20 as determined by the physician. The peel away needle introducer 70 includes a needle 74 defining an introducer channel 72 which extends the length of the needle 74 and a peel away Teflon sheath 76. As used in conjunction with the present invention, and best shown in FIG. 5, the needle introducer 70 is introduced into the wound bed 20 followed by removal of the needle 74 (not shown), which leaves the sheath 76 remaining embedded in the wound bed 20. FIG. 6 illustrates insertion of the hollow fiber catheter 50a, 50b into the sheath 76, thereby introducing the hollow fiber catheter 50a, 50b into the wound bed 20 at an advantageous position as determined by the physician. The sheath 76 is next removed (not shown) resulting in the hollow fiber catheter 50a, 50b in position for treatment.

In one embodiment, the semi-permeable membrane can be made from a hollow fiber 52. Suitable materials for use as hollow fibers 52 of the present invention provide an optimal combination of such properties as mass transfer properties, biocompatibility, surface-to-volume ratio, processability, hydrophobicity/hydrophilicity, strength, transport rate, and porosity. Examples of suitable hollow fibers are described in, for instance, I. Cabasso, "Hollow-Fiber Semi-Permeable membranes", pp 598-599 in *Kirk Othmer Concise Encyclopedia of Chemical Technology*, which section is herein incorporated in its entirety. Hollow fibers 52 as used in the present invention are made by Minntech Corporation, Plymouth, Minn., from an extruded polymeric dope mixture of polysulfone and polyvinyl pyrrolidone dissolved in an aprotic solvent. The physical morphology of the hollow fiber 52 is rapidly formed by passing the polymeric dope mixture through an outer annular orifice of a tube-in-orifice spinneret while simultaneously passing a precipitating solution through the central tube of the spinneret. The emerging hollow fiber 52 travels substantially downward for about 0.01-10 m before submersion into a quenching bath. See U.S. Pat. No. 5,762,798 to Wenthold et al., which is herein incorporated by reference in its entirety.

Figure 11:
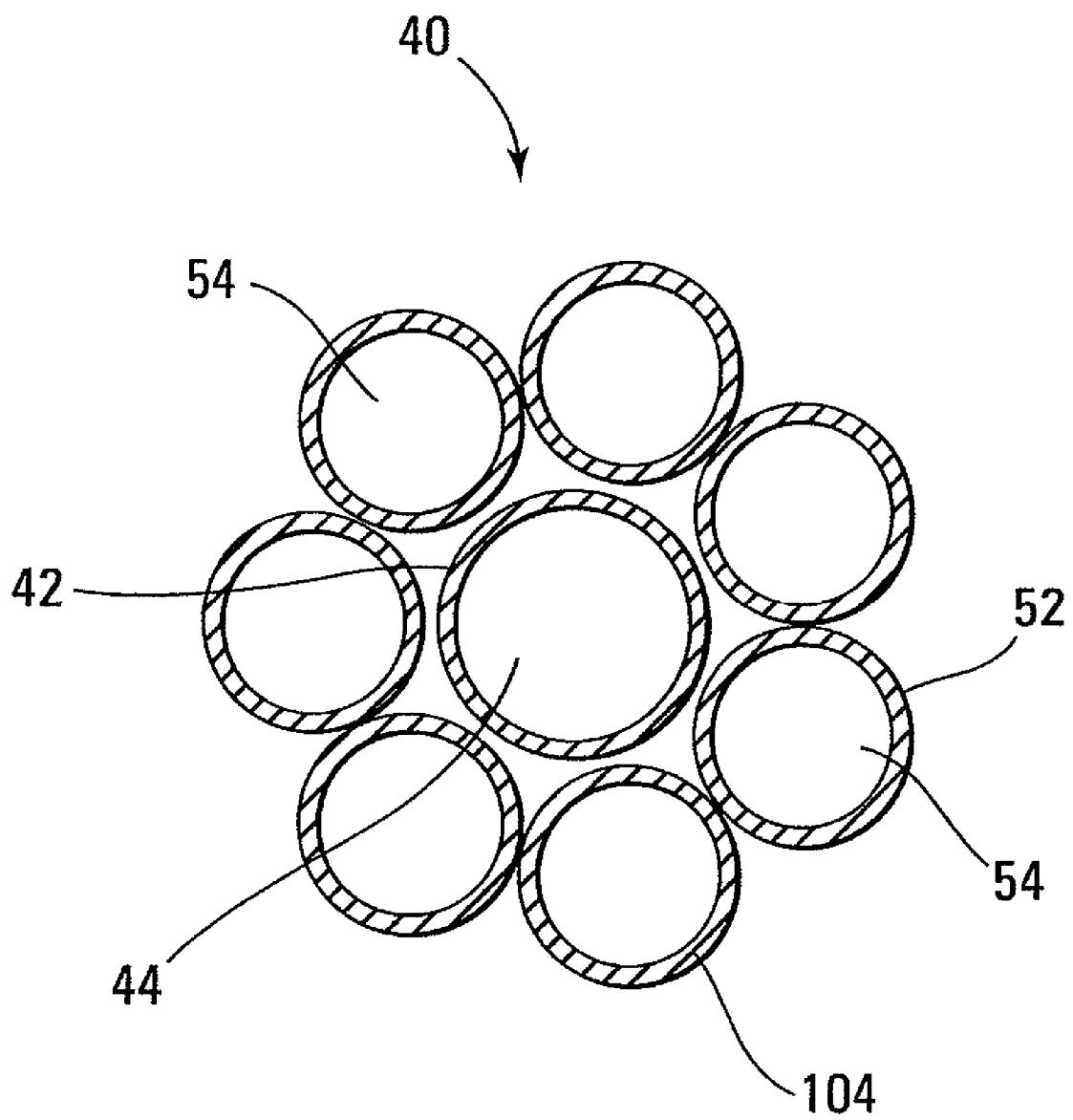
FIG. 11 is a lateral cross section of a hollow fiber bundle.

As used in the present invention, the hollow fiber 52 when used for fluid aspiration can range in diameter between approximately 200 μm to 800 μm. Pore size when used for aspiration is approximately 0.1 μm, which prevents the uptake of unintended components such as cells and prevents generation force that would injure or distort the tissue. As best shown in FIG. 11, the hollow fiber bundle 40 used for aspiration has a diameter of approximately 1.6 mm. When used for drug delivery or infusion, the hollow fiber 52 ranges in diameter between approximately 200 μm to 800 μm in diameter. Pore size ranges in hollow fiber catheters 50b used for infusion can vary between approximately 0.1 μm to 1.0 μm, in most cases approximately 0.45 μm, which can be larger than when used for aspiration, because the delivered substance is presumably of known composition and homogeneous in consistency and size. The length of the hollow fiber 52 portion of the hollow fiber catheter 50a, 50b ranges between approximately 2 to 10 cm. It should be noted that the ranges given here are used for purposes of illustration only and are not intended to be so limiting. Other ranges would also be effective and are therefore are within the scope of the invention.

In another embodiment, the semi-permeable membrane can be a modified microcatheter. Modified microcatheters can be prepared in any suitable manner, e.g., by microperforating an otherwise intact capillary or by spinning hollow fiber semi-permeable membranes from natural or synthetic polymers. Such fibers can be formed having any desired characteristics, e.g., isotropic (dense or porous) and anisotropic (asymmetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like. Other examples of suitable materials include membrane fibers such as those identified in the following table:

| Types | Manufacturer | Catalog No. | Interior Diameter (um) | Wall Thickness (um) | Flow Rate (mL/min)/ Surface Area (sq. meter) | Porosity |
|---|---|---|---|---|---|---|
| Cuprophan | Baxter Haemodialysis Products | unknown | 200 | 8 | unknown | |
| Hemophan FoCus 160-H | Baxter Haemodialysis Products | unknown | 200 | 8 | unknown | |
| Spectra/Por Regenerated Cellulose Polyethylene Polypropylene Polysulfone | Spectrum 23022 La Cadena Drive, Suite #100 Laguna Hills, Ca. 92653 | #132-200 through 132-313 membrane types vary according to m.w., volume, pH, and chemical compatibility | 200 380 500 | 10-20 25 75 | 25-15 | 0.5 um 50 nm |
| Cellulose Triacetate CT-190 | Baxter Haemodialysis Products | CT-190 series #5M1546 CT-110-190 also available | 200 | unknown | unknown | |
| Cellulose Acetate CA-170 | Baxter Haemodialysis Products | CA-170 series #5M-1735 CA-150-CA-170 series also available | unknown | unknown | unknown | |

-continued

| Types | Manufacturer | Catalog No. | Interior Diameter (um) | Wall Thickness (um) | Flow Rate (mL/min)/ Surface Area (sq. meter) | Porosity |
|---|---|---|---|---|---|---|
| Polysulfone Hemoflow F-60A High Flux | Fresenius | F60 series #0500136A F3-6, 8, 40-80 series also available | 200 | 40 | 40/1.3 | |
| Polysulfone Polyphen Capillary Membrane | Minntech | | 280 | 40 | | 0.45 um 0.10 um |
| Polyacrylonitrile (PAN) | Gambro-Health | | unknown | unknown | unknown | |
| Polyimide | UBE | unknown | unknown | unknown | unknown | unknown |
| Polysulfone | GE Healthcare | unknown | 0.5 mm (.45 um) 0.75 mm (.65 um) | unknown | unknown | 500,000 mwco |
| PVDF Polysulfone PAN | Koch | Unknown Unknown unknown | 0.5 mm & larger .043 inch | unknown | unknown | Up to 0.2 um Up to 500,000 mwco |
| PES-phylic-phobic PVDF | Membrana | Unknown Unknown unknown | 300 350 unknown | 100 85 unknown | unknown | 0.5 um 0.5 um unknown |
| PVDF PP | Memcor/US filter | Unknown unknown | 500 unknown | 150 unknown | unknown | 0.04 to 0.1 um 0.1 um |

Figure 7:
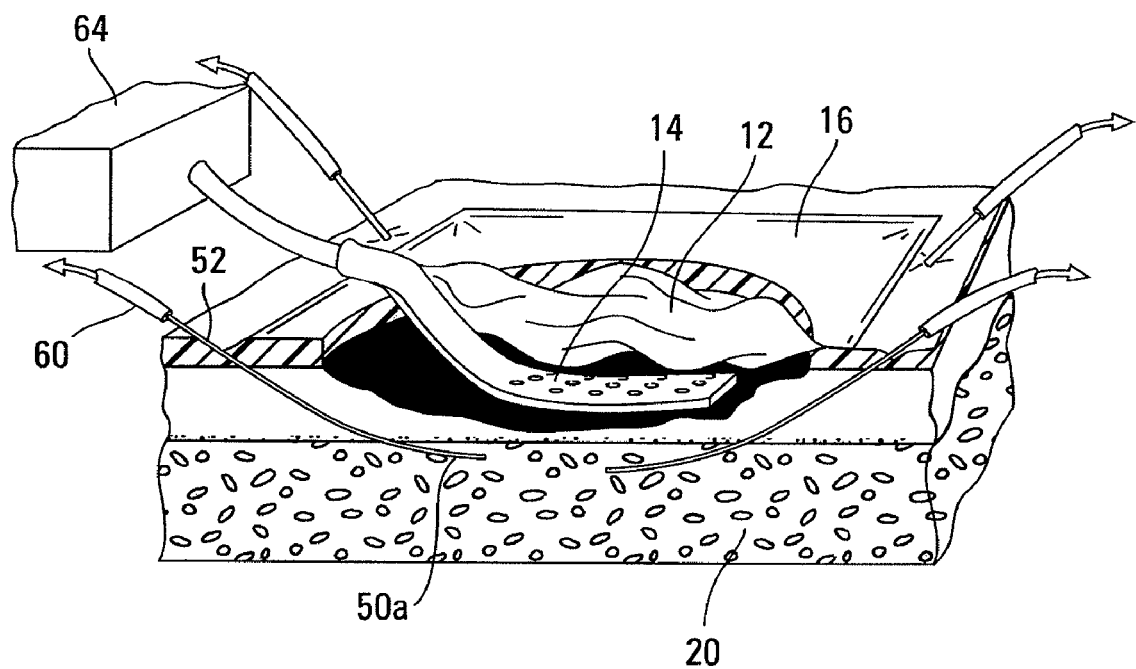
FIG. 7 is a perspective view of negative pressure applied to a hollow fiber catheter of the present invention in conjunction with conventional negative pressure therapy for wound care.

FIG. 7 illustrates an embodiment of the present invention in which hollow fiber catheters 50a are used in combination with conventional topical negative pressure (TNP) which is shown here represented by a relatively large conventional drainage catheter 14 which is typically 5 mm to 10 mm in diameter. Depending on the nature of the wound, an incision may be required to be created through the wound, through which the drainage catheter 14 is inserted and then covered and sealed with an open weave cotton gauze 12 and wound care film 16. In other cases, the drainage catheter 14 is inserted directly onto the wound, followed by placement of open weave cotton gauze 12 followed by a layer of wound care film 16. A vacuum pump 64 is connected to the drainage catheter 14 in order to apply negative pressure topically. The effective area of negative pressure is confined to the wound area by the wound care film 16. Topical negative pressure is used to remove excess tissue fluid, which promotes healing and also applies a closure force to further accelerate wound healing. Following placement of the drainage catheter 16 at least one and possibly several hollow fiber catheters 50a are inserted into the wound bed 20 and connected with the vacuum pump 64, as best shown in FIG. 1. It is contemplated that the drainage catheter 14 and hollow fiber catheters 50a are each attached to the same vacuum pump 64, however, separate vacuum pumps (not shown) are also within the scope of the invention. A control monitor 150 as shown in FIG. 10 has a single vacuum pump 64 which is in fluid communication with separate vacuum pump regulators 170, 172 for the drainage catheter(s) 14 and hollow fiber catheter(s) 50a respectively. The vacuum pump regulator (drainage catheter) 170 is provided with a plurality of vacuum pump inputs 170a, 170b, 170c, 170d to accommodate a plurality of drainage catheters 14. Similarly, the vacuum pump regulator (hollow fiber catheter) 172 is provided with a plurality of vacuum pump inputs 172a, 172b, 172c, 172d to accommodate a plurality of hollow fiber catheters 50a. Either simultaneously or after initiation of topical negative pressure being applied to the drainage catheter 14, negative pressure is also applied to the hollow fiber catheter(s) 50a which further facilitates the wound healing process by removing tissue fluid from the tissues of the wound bed 20 beneath the wound surface (unnumbered). Those skilled in the art will understand that hollow fiber catheters 50a can thus be used beneficially on the tissue that will ultimately determine, at least in part, how the wound will heal.

Figure 8:
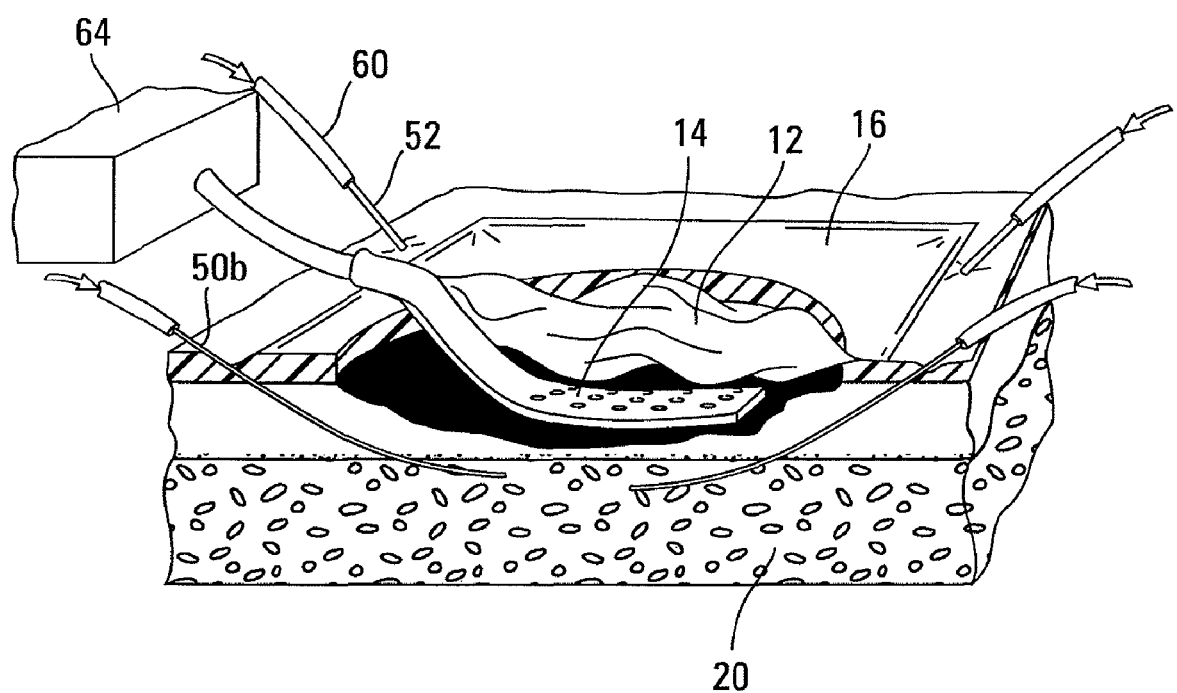
FIG. 8 is a perspective view of positive pressure applied to a hollow fiber catheter of the present invention in conjunction with conventional negative pressure therapy for drug delivery.

FIG. 8 illustrates an embodiment of the present invention wherein hollow fiber catheters 50b are used for infusion or drug delivery in combination with conventional topical negative pressure (TNP) which is shown here represented by a relatively large conventional drainage catheter 14 which is typically 5 mm to 10 mm in diameter. Depending on the nature of the wound, an incision may required to be created through the wound, through which the drainage catheter 14 is inserted into the wound bed 20 and then covered and sealed with an open weave cotton gauze 12 and wound care film 16. In other cases, the drainage catheter 14 is inserted directly onto the wound, followed by placement of open weave cotton gauze 12 followed by a layer of wound care film 16. A vacuum pump 64 is connected to the drainage catheter 14 in order to apply negative pressure topically. The effective area of negative pressure is confined to the wound area by the wound care film 16. Topical negative pressure is used to remove excess tissue fluid, which promotes healing and also applies a closure force to further accelerate wound healing. Following placement of the drainage catheter 16 at least one and possibly several hollow fiber catheters 50b are inserted into the wound bed 20 and connected with an infusion pump 100, as best shown in FIG. 1A. Prior to introduction of the hollow fiber catheters 50a, a conventional peel away needle introducer 70 as shown in FIG. 4 is inserted into the wound bed 20 as determined by the physician. The hollow fiber catheters 50b are connected to and in fluid communication with the infusion pump 100 which is in fluid communication via an infusion line 102 with an infusion reservoir 104. The infusion reservoir 104 contains a therapeutic fluid 106 which is distributed, using positive fluid pressure from the infusion pump 100, to the wound bed 20 underlying the wound. Different therapeutic fluids 106 can be precisely distributed to areas of the wound bed 20 requiring treatment, including but not limited to normal saline, antibiotics, growth factors, anesthetics, or other pain medication. One of the advantages of using hollow fiber catheters 50b to deliver therapeutic fluids 106 to the wound bed 20 is an ability to provide a much wider and more even distribution of therapeutic fluids 106 to the wound bed 20 and better penetration into the tissues than can be achieved by the topical application of therapeutic fluids 106 alone. A control monitor 150 as shown in FIG. 10 has a single vacuum pump 64 which is in fluid communication with separate vacuum pump regulator 170 for the drainage catheter(s) 14 and hollow fiber catheters 50b respectively. The vacuum pump regulator (drainage catheter) 170 is provided with a plurality of vacuum pump inputs 170a, 170b, 170c, 170d to accommodate a plurality of drainage catheters 14. The control monitor 150 also has a single infusion pump 100 which is in fluid communication with a plurality of infusion pump outlets 100a, 100b, 100c, 100d so as to accommodate a plurality of hollow fiber catheters 50b used for infusion or drug delivery.

Figure 9:
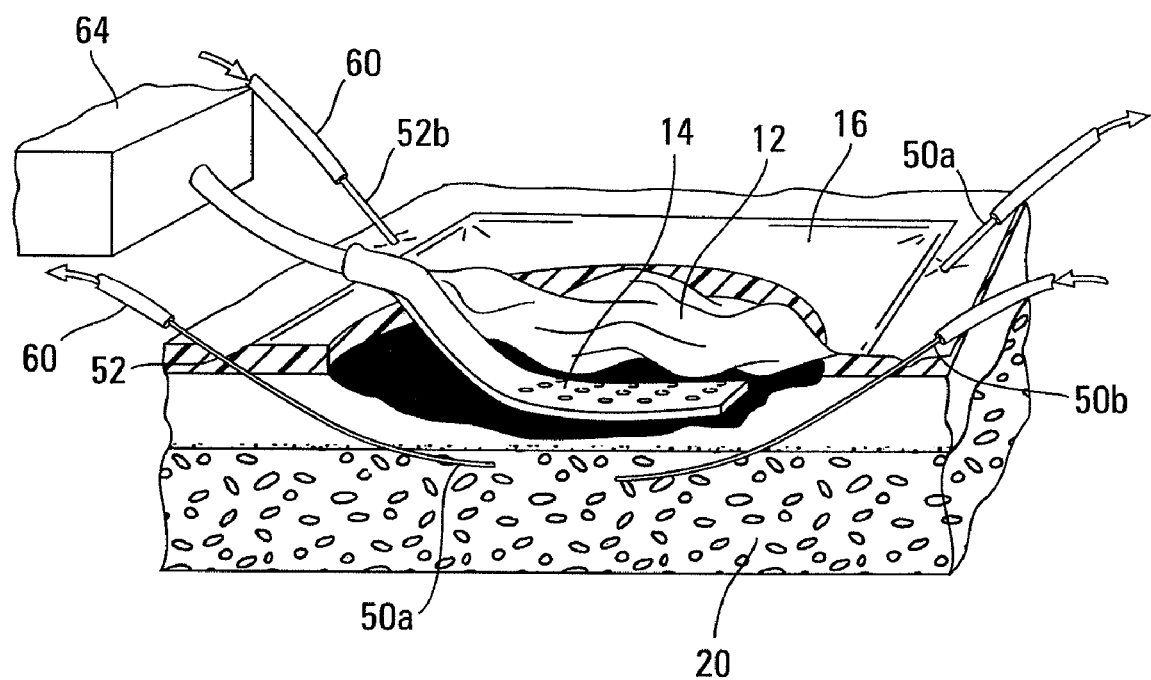
FIG. 9 is a perspective view of one set of hollow fiber catheters having negative pressure applied and another set of hollow fiber catheters having positive applied, to simultaneously remove fluid and deliver therapeutic liquids to a wound area.

FIG. 9 illustrates an embodiment of the present invention wherein hollow fiber catheters 50a, 50b are used in combination with conventional topical negative pressure (TNP) which is shown here represented by a relatively large conventional drainage catheter 14 which is typically 5 mm to 10 mm in diameter. Depending on the nature of the wound, an incision may required to be created through the wound, through which the drainage catheter 14 is inserted and then covered and sealed with an open weave cotton gauze 12 and wound care film 16. In other cases, the drainage catheter 14 is inserted directly onto the wound, followed by placement of open weave cotton gauze 12 followed by a layer of wound care film 16. A vacuum pump 64 is connected to the drainage catheter 14 in order to apply negative pressure topically. The effective area of negative pressure is confined to the wound area (unnumbered) by the wound care film 16. Topical negative pressure is used to remove excess tissue fluid, which promotes healing and also applies a closure force to further accelerate wound healing. Prior to introduction of the hollow fiber catheters 50a a conventional peel away needle introducer 70 as shown in FIG. 4 is inserted into the wound bed 20 as determined by the physician. It is contemplated that the drainage catheter 14 and hollow fiber catheters 50a are each attached to the same vacuum pump 64, however, separate vacuum pumps (not shown) are also within the scope of the invention. Following placement of the drainage catheter 16 at least a first 50a and a second 50b and possibly several hollow fiber catheters 50a, 50b are inserted into the wound bed 20. The first set of the hollow fiber catheters 50a is connected to and in fluid communication with the vacuum pump 64, which provides negative pressure to enhance tissue fluid removal from the wound bed 20 and thus improve the wound healing process over the conventional method. It is contemplated that the drainage catheter 14 and hollow fiber catheters 50a are each attached to the same vacuum pump 64, however, separate vacuum pumps (not shown) are also within the scope of the invention. Either simultaneously or after initiation of topical negative pressure being applied to the drainage catheter 14, negative pressure is also applied to the hollow fiber catheters 50a which further facilitate the wound healing process by removing tissue fluid. The second set of hollow fiber catheters 50b is in fluid communication with and connected to an infusion pump 100, as best shown in FIG. 1A. The infusion pump 100 is in fluid communication via an infusion line 102 with an infusion reservoir 104. The infusion reservoir 104 contains a therapeutic fluid 106 which is distributed, using positive fluid pressure from the infusion pump 100, to the wound bed 20 underlying the wound. Different therapeutic fluids 106 can be precisely distributed to areas of the wound bed 20 requiring treatment, including but not limited to normal saline, antibiotics, growth factors, anesthetics, or other pain medication. Using the first set of hollow fiber catheters 50a connected to the vacuum pump 64 in simultaneously with the second set of hollow fiber catheters 50b to deliver therapeutic fluids 106 to precise locations in the wound bed 20 can provide an enhancement over conventional negative pressure wound care treatment techniques.

FIG. 10 illustrates a schematic of a control unit/monitor 150 which is used in conjunction with the methods described above. A power switch 156 is in electrical communication with a battery pack 160 which provides a source of electrical energy to the control unit/monitor 150 and is itself in electrical communication with an isolation transformer power supply 162 which conditions the electrical energy to a form suitable for use. An AC power unit 158 is in electrical communication with a power cord 155 and supplies electrical energy to recharge the battery pack 160. A central processing unit 164 (CPU) is in electrical communication with the display 152 and user input 154 which allows the user to simultaneously monitor results and make control inputs as necessary for the particular procedure. The central processing unit 164 is also in electrical communication with a sensor processor 166 which can be adapted to receive signals from a variety of sensors placed in the hollow fiber catheter(s) 50a, 50b, including but not limited to parameters such as internal pressure, temperature, oxygen levels and potassium levels. The control unit/monitor 150 also comprises the vacuum pump 64, vacuum pump regulator (drainage catheter) 170, vacuum pump regulator (hollow fiber) 172, infusion pump 100 and infusion pump regulator 108. The control unit/monitor 150 has a single vacuum pump 64 which is in fluid communication with separate vacuum pump regulators 170, 172 for the drainage catheter(s) 14 and hollow fiber catheters 50a respectively. The vacuum pump regulator (drainage catheter) 170 is provided with a plurality of vacuum pump inputs 170a, 170b, 170c, 170d to accommodate a plurality of drainage catheters 14. Similarly, the vacuum pump regulator (hollow fiber catheter) 172 is provided with a plurality of vacuum pump inputs 172a, 172b, 172c, 172d to accommodate a plurality of hollow fiber catheters 50a. It is also seen that the control monitor 150 also has a single infusion pump 100 which is in fluid communication with a plurality of infusion pump outlets 100a, 100b, 100c, 100d so as to accommodate a plurality of hollow fiber catheters 50b used for infusion or drug delivery.

Infusion through each pump outlet 100 is preferably controlled so that all hollow fiber catheters 50b receive an equal amount of fluid and drug. If one line is in low resistant tissue, then more fluid may be delivered to that line at the expense of delivery to the other lines. Methods to equalize fluid delivery to all lines include using a separate pump for each line, using an electrical or mechanical device to alternate fluid pathways so that each line gets an equal infusion volume.

Another embodiment is shown in FIGS. 12 and 13. A high pressure pump can deliver fluid to each catheter, wherein each catheter has a resistor that limits flow to each catheter. As an example, a pump can deliver fluid at 50 mmHg through a resistor that is 150 microns in diameter for a length of 10 cm. Pressure at the distal end of the resistor will be approximately 42 mmHg, and flow through the resistor will be approximately 2 ul/min. Flow out of the hollow fiber catheter usually requires much lower pressure than 42 mmHg, so ultimately delivery will be volume/flow controlled.

In another embodiment, the infusion pump can monitor pressure, and through a servocontrol mechanism, maintain constant pressure at the designated pressure, perhaps between a range of 20-100 mmHg. Furthermore, the volume delivered by the pump can be monitored to assume total drug deliver.

Finally, at least a single USB port 168 is provided which allows a USB memory stick (not shown) to collect data to be used for analysis at a different time or location.

In one aspect, the invention comprises a system and corresponding kits including a vacuum pump 64, a drainage catheter 14, open weave cotton gauze 12, wound care film 16, at least one and preferably a plurality of needle introducers 70 and at least one and preferably a plurality of hollow fiber catheters 52*a*, 52*b*. In another aspect, the invention comprises a system and corresponding kits including a vacuum pump 64, an infusion pump 100, a drainage catheter 14, open weave cotton gauze 12, wound care film 16, at least one and preferably a plurality of needle introducers 70 and at least one and preferably a plurality of hollow fiber catheters 52*a*, 52*b*. In yet another aspect, the invention comprises a system and corresponding kits including a control monitor unit 150, a drainage catheter 14, open weave cotton gauze 12, wound care film 16, at least one and preferably a plurality of needle introducers 70 and at least one and preferably a plurality of hollow fiber catheters 52*a*, 52*b*.

It should be mentioned that it is contemplated by and therefore within the scope of the invention to provide hollow fiber catheters adapted for additional functions. For example, sensor signal transmitters (not shown) could be placed at the distal tip 52*a*, 52*c* of the hollow fiber catheter 50*a*, 50*b* capable of determining parameters such as internal pressure, temperature, oxygen levels and potassium levels. The sensor signal transmitters (not shown) (electrical leads or optical fibers) could also serve as the stylet 56. Various biomarkers could be determined from analyzing the withdrawn fluid, such as K lactate levels and proteins. Additionally, sensors could be added to hollow fiber catheters to sense electrical impedance, which would provide information which could alter the course of treatment. These sensors (not shown) and/or biomarkers would be used to stage the wound care treatment, providing a diagnostic tool to determine the need for increased or decreased therapeutic intensity such as more drug and/or fluid removal. A further improvement is the incorporation of a heating element within the hollow fiber 52 as heat is known to have a beneficial effect on wound healing in some cases. Among other methods of delivering heat is through the transmission of RF (radio frequency) energy through the hollow fiber catheter via an incorporated electrode (not shown).

As best shown in FIGS. 12-13 another embodiment to be used with the control unit/monitor 150 which is used to further control the flow rate through the infusion lines 100*a*, 100*b*, 100*c*, 100*d*. As an example, the infusion pump 100 delivers fluid at about 50 mmHg through the infusion line 100*a*, 100*b*, 100*c*, 100*d* that is approximately 150 microns in diameter for a length of approximately 10 cm. Pressure at the distal end of the infusion line 100*a*, 100*b*, 100*c*, 100*d* will be approximately 42 mmHg and flow through the infusion line 100*a*, 100*b*, 100*c*, 100*d* approximately 2 ul/min. Flow out of the hollow fiber catheter 50*b* usually requires much lower pressure than 42 mmHg, so ultimately delivery will be volume/flow controlled. FIG. 13 shows a more detailed view of the high pressure infusion line 96 and its relationship to the infusion line 100*a*, 100*b*, 100*c*, 100*d* and hollow fibers 50*b*. It can be seen that the line is adapted to provide a constricted region adapted to serve as a resistor in order to reduce pressure and provide a lower pressure system or area.

What is claimed is:

1. A method comprising performing topical negative pressure wound care while simultaneously infusing a therapeutic fluid into the wound, the method further comprising:
   a. providing one or more drainage catheters and one or more hollow fiber catheters;
   b. positioning the one or more drainage catheters and one or more hollow fiber catheters proximate a wound bed and in desired positions relative to each other, the one or more hollow fiber catheters being embedded in tissue underlying the wound, in a manner sufficient to permit the hollow fibers to deliver therapeutic fluid to the wound bed using positive fluid pressure;
   c. connecting the drainage catheter(s) to a vacuum pump and activating the vacuum pump to draw a vacuum from the drainage catheter(s);
   d. connecting the hollow fiber catheter(s) to an infusion pump which is connected to and in fluid communication with the therapeutic fluid and activating the infusion pump to apply positive fluid pressure to the hollow fiber catheter(s), thus delivering the therapeutic fluid through the hollow fiber catheter(s).

2. A method according to claim 1 wherein the hollow fiber catheter(s) are positioned by introducing a needle introducer having a needle covered by a peel away sheath into the wound bed, removing the needle and inserting a hollow fiber catheter into the peel away sheath, followed by removing the sheath, leaving the hollow fiber catheter in place.

3. The method according to claim 1 wherein an incision is created proximate the wound area prior to introducing the drainage catheter into the incision.

4. The method according to claim 1 wherein the drainage catheter is placed onto the surface of the wound.

5. A method according to claim 1, further comprising providing one or more additional hollow fiber catheters embedded in the tissue and used for aspiration of fluid from the tissue site.

6. A method according claim 5, wherein the therapeutic fluid is selected from the group consisting of saline, antibiotics, growth factors, anesthetics, and pain medication.

7. A method according to claim 5 wherein the therapeutic fluid is infused at positive pressure of between about 20-100 mm Hg.

8. A method according to claim 5 wherein one or more of the hollow fiber catheters are adapted with a sensor signal transmitter placed at the distal tip.

9. A method according to claim 5 wherein the sensor is capable of determining a parameter selected from the group consisting of internal pressure, temperature, oxygen level, and potassium level.

10. A method according claim 1, wherein the therapeutic fluid is selected from the group consisting of saline, antibiotics, growth factors, anesthetics, and pain medication.

11. A method according to claim 1 wherein the therapeutic fluid is infused at positive pressure of between about 20-100 mm Hg.

12. A method according to claim 1 wherein one or more of the hollow fiber catheters are adapted with a sensor signal transmitter placed at the distal tip.

13. A method according to claim 1 wherein the sensor is capable of determining a parameter selected from the group consisting of internal pressure, temperature, oxygen level, and potassium level.

14. A method comprising performing topical negative pressure wound care while simultaneously infusing a therapeutic fluid into the wound, comprising:
  a. providing one or more drainage catheters, at least a first hollow fiber catheter used for aspiration of fluid and at least a second hollow fiber catheter for infusion of the therapeutic fluid;
  b. positioning the one or more drainage catheters, one or more first hollow fiber catheter and the at one or more second hollow fiber catheters proximate a wound bed, embedded in tissue underlying the wound and in desired positions relative to each other;
  c. connecting the drainage catheter(s) to a vacuum pump and first hollow fiber catheter(s) to a vacuum pump and activating the vacuum pump to provide negative pressure to both the drainage catheter(s) and hollow fiber catheter(s) in a desired manner;
  d. connecting the second hollow fiber catheter(s) to an infusion pump which is connected to and in fluid communication with the therapeutic fluid and activating the infusion pump to apply positive fluid pressure to the hollow fiber catheter(s), thus delivering the therapeutic fluid through the hollow fiber catheter(s).

15. A method according to claim 14 wherein the hollow fiber catheter(s) are positioned by introducing a needle introducer having a needle covered by a peel away sheath into the wound bed, removing the needle and inserting a hollow fiber catheter into the peel away sheath, followed by removing the sheath, leaving the hollow fiber catheter in place.

16. A method according to claim 14 wherein the drainage catheter is placed onto the surface of the wound.

17. A method according claim 14, wherein the therapeutic fluid is selected from the group consisting of saline, antibiotics, growth factors, anesthetics, and pain medication.

18. A method according to claim 14 wherein the therapeutic fluid is infused at positive pressure of between about 20-100 mm Hg.

19. A method according to claim 14 wherein one or more of the hollow fiber catheters are adapted with a sensor signal transmitter placed at the distal tip.

20. A method according to claim 14 wherein the sensor is capable of determining a parameter selected from the group consisting of internal pressure, temperature, oxygen level, and potassium level.

* * * * *